US007027165B2

(12) United States Patent
De Haas et al.

(10) Patent No.: US 7,027,165 B2
(45) Date of Patent: Apr. 11, 2006

(54) METHOD AND DEVICE FOR SURFACE EVALUATION

(75) Inventors: Klaas Hendrik De Haas, Woerden (NL); Gerrit Cornelis Dubbeldam, Zevenaar (NL); Ivo Bernardus Nicolaas Van Der Lans, Den Hoorn (NL); Robin Paul Fries, Zoetermeer (NL)

(73) Assignee: Akzo Nobel N.V., Arnhem (NL)

( * ) Notice: Subject to any disclaimer, the term of this patent is extended or adjusted under 35 U.S.C. 154(b) by 148 days.

(21) Appl. No.: 10/117,636

(22) Filed: Apr. 5, 2002

(65) Prior Publication Data

US 2002/0176093 A1 Nov. 28, 2002

Related U.S. Application Data

(60) Provisional application No. 60/291,046, filed on May 15, 2001.

(30) Foreign Application Priority Data

Apr. 6, 2001 (EP) .................................. 01201276

(51) Int. Cl.
*G01B 11/24* (2006.01)
*G01B 11/30* (2006.01)
(52) U.S. Cl. ...................................... 356/600; 356/601
(58) Field of Classification Search ........ 356/600–601, 356/237.1–237.6
See application file for complete search history.

(56) References Cited

U.S. PATENT DOCUMENTS

| 4,846,578 A | * | 7/1989 | Morita et al. ................ 356/446 |
| 5,078,498 A | | 1/1992 | Kadakia et al. ............. 357/23.4 |
| 5,550,632 A | | 8/1996 | Harata ......................... 356/446 |
| 5,640,237 A | | 6/1997 | Esrig et al. .................. 356/237 |
| 5,850,472 A | | 12/1998 | Alston et al. ................ 382/162 |
| 5,909,276 A | * | 6/1999 | Kinney et al. ............ 356/237.2 |
| 5,946,029 A | | 8/1999 | Yoshimura et al. .......... 348/131 |
| 6,509,964 B1 | * | 1/2003 | Wiles et al. .............. 356/237.2 |

OTHER PUBLICATIONS

"Method for Measuring Glossiness of Spherical Surfaces Utilizing Brightness Pattern of Image". Kugisawa et al. IEICE Transactions. pp. 2655-2662 vol. E 74 No. 9. (1991).
Color Technology for Electronic Imaging Devices. Chapter 3 Regression. SPIE Optical Engineering Press. H.R. Kong, pp. 55-63 (1997).
Color Technology for Electronic Imaging Devices. Chapter 11 Color Input Devices. SPIE Optical Engineering Press. H.R. Kong, pp. 272-294 (1997).
European Search Report for EP 01 20 1276 dated: Sep. 4, 2001.

* cited by examiner

Primary Examiner—Gregory J. Toatley, Jr.
Assistant Examiner—Amanda Merlino
(74) Attorney, Agent, or Firm—Joan M. McGillycuddy; Michelle J. Burke

(57) ABSTRACT

Device and method for recording the visual properties of a surface, comprising an imaging device for recording light interaction (reflection or transmission) with a surface, a light source, and a sample area for positioning a sample with a surface to be examined. The imaging device, the light source, and the sample area are arranged in such a way that in one image at least one of the surface properties is recordable as a function of a continuous range of angles between the illumination direction and the observation direction. The imaging device is a CCD camera. The device and method are suitable for imaging and evaluating visual properties which are dependent on the optical geometry, such as flop behavior and gloss.

11 Claims, 6 Drawing Sheets

METHOD AND DEVICE FOR SURFACE EVALUATION

Figure 1:
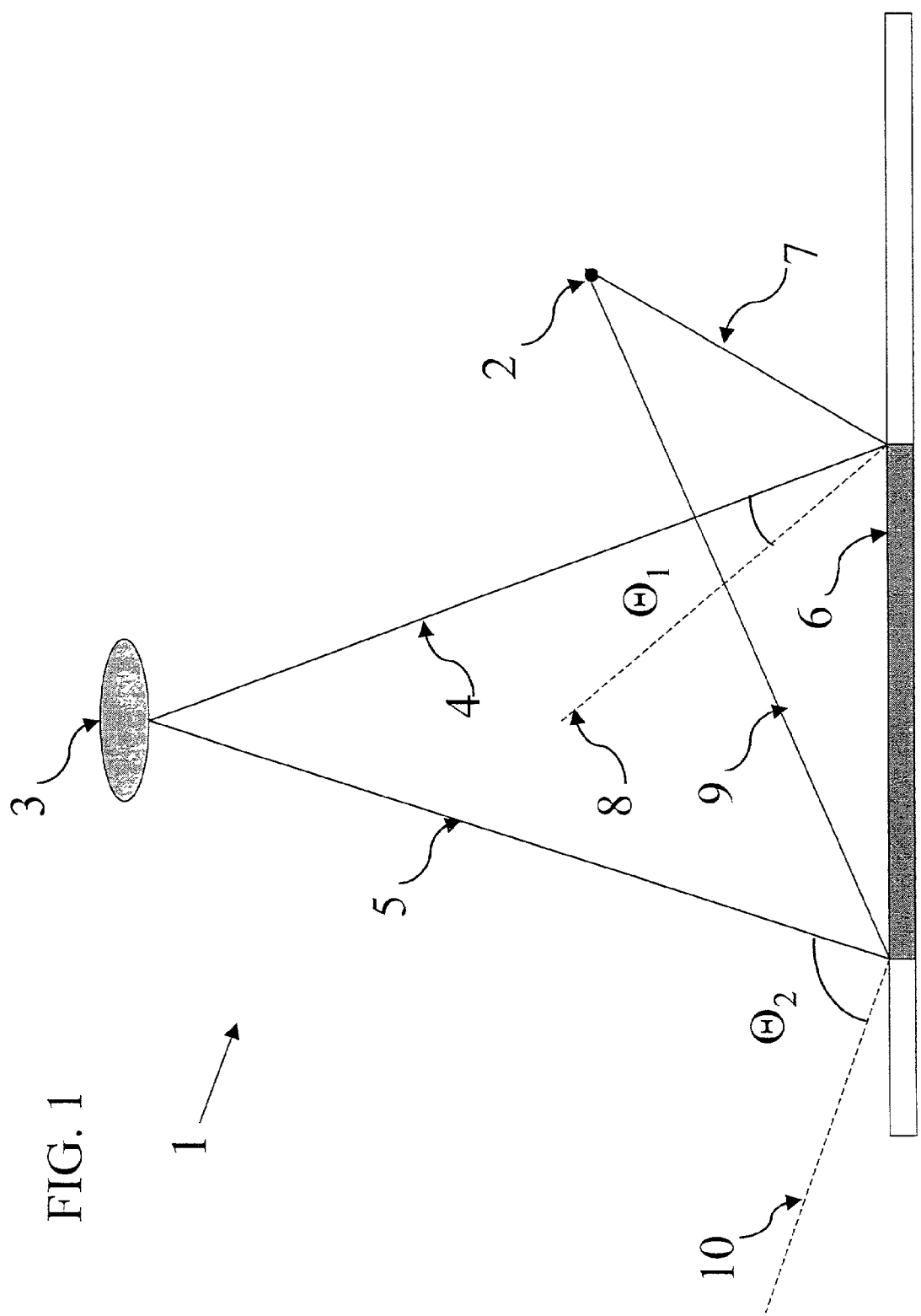

This application claims priority of European Patent Application No.: 01201276.1, filed on Apr. 6, 2001 and also claims priority of U.S. Patent Application No.: 60/291,046, filed on May 15, 2001.

FIELD OF THE INVENTION

The invention relates to a method and a device for recording the visual properties of a surface, for example the colour, gloss, texture, etc. of pigmented coating films, using an imaging device, a light source, and a sample area for positioning a sample with a surface to be examined. The visual appearance of a surface can be dependent on optical geometry, optical geometry being defined as the positioning of an observed object relative to an observer and a light source. This dependency can occur for example in films of coatings comprising effect pigments. The dependency of visual properties on optical geometry is generally called goniochromatism, or flop behaviour. In optical geometry, the observation direction is the line between the observer and an observed point on the observed object, and the illumination direction is the line between the light source and the observed point. The aspecular direction is the direction of a line mirroring the illumination direction by a mirror plane perpendicular to the sample surface. The flop angle, also called the aspecular angle, is the angle between the observation direction and the specular direction. Also gloss, of either effect or non-effect films, is dependant on the optical geometry.

BACKGROUND OF THE INVENTION

Effect pigments are used in coatings to obtain optical effects, such as a metallic or pearlescent look. Typically, in a film of a coating comprising metallic pigments lightness is dependent on the optical geometry, whereas with coatings comprising pearlescent pigments the hue changes with the optical geometry. This complicates the characterization of the visual appearance of such coating films. A further complication in this respect is the appearance of local strong scattering spots in the coating film when it is observed from a short distance, due to the presence of pigment flakes. Whereas a solid colour can be wherein by the spectral distribution of reflectance values, coatings comprising effect pigments require taking the angular and spatial dependency into account. Hitherto, the dependency of the lightness and colour of metallic and pearlescent coatings on optical geometry was examined by using a spectrophotometer at a limited number of different measuring geometries. However, this results in an incomplete picture giving data at only a very limited number of optical geometries.

U.S. Pat. No. 5,550,632 discloses a method and an arrangement for evaluating paint films using a digital photo camera. Only one optical geometry is used per recording, and since the camera is focussed, only one flop angle. Since the appearance of a coating layer comprising effect pigments is dependent on the flop angle, this method cannot be used for the evaluation of such effect coatings in one recording.

SUMMARY OF THE INVENTION

The object of the invention is a system allowing the evaluation of a surface in a single recording over a continuous range of flop angles.

Additionally, the object of the invention is a device for recording the visual properties of a surface, comprising an imaging device for recording light interaction with a surface, a light source, and a sample area for positioning a sample with a surface to be examined. The imaging device, the light source, and the sample area are arranged in such a way that in one image at least one of the surface properties is recordable as a function of a continuous range of angles between the illumination direction and the observation direction.

A further object of the invention is achieved by a device for recording the flop angle dependent properties of a surface, comprising an imaging device for recording light interaction by a surface, a light source, and a sample area for positioning a sample with a surface to be examined, wherein in that the scope of the imaging device covers a continuous range of observation directions and in that the imaging device, the light source, and the sample area are arranged in such a way that in one image at least one of the surface properties is recorded as a function of the flop angle. The recording can be used for visual inspection and comparison or, depending on the capability of the imaging device to quantify recorded signals, for measurement or data processing. Particular examples of use are gloss measurement and colour matching.

DETAILED DESCRIPTION OF THE INVENTION

A device or arrangement according to the present invention is particularly suitable for evaluating the flop behaviour, or goniochromatism, of a surface coated with a coating containing effect pigments.

To get a useful picture of flop behaviour, the range of flop angles, as defined above, should preferably span more than 40 degrees, more preferably more than 50 degrees.

For some types of surfaces, such as coating films containing metallic pigments, the colour is darker at larger flop angles. To utilize the full measurement range in such a case, the light distribution is preferably varied over the viewing scope of the imaging device, preferably according to an increasing or decreasing function. This function is dependent on the type of material. The light distribution can be varied by varying the light output of the light source as a function of the illumination angle. Alternatively, the light distribution can be varied by using suitable filters.

In a preferred arrangement, the light source can be a line source, such as a TL strip light, a horizontal slit in a light diffusor, an array of point sources, such as LEDs or glass fibres, etc. Alternatively, the light source may be a point source.

A suitable imaging device in an arrangement according to the invention is a CCD camera, or Charge Coupled Device camera. Suitable CCD photo cameras are for instance the Ricoh® RDC 5000, the Olympus® C-2000Z, the Minolta® Dimage® RD 3000, and the Nikon® Coolpix® 950.

Digital video cameras form another group of suitable devices which can be used to implement the present invention. Using a video camera the flop angle can be varied not only as a function of location, but, alternatively or additionally, as a function of time. Using a video camera also makes it possible to monitor time-dependent changes in the visual appearance of the examined surface over a period of time, for instance the appearance of a coating film during curing.

Using a digital camera, every recorded image is composed of a large number of pixels. Every pixel has a red value R, a green value G, and a blue value B. Ideally, calibrated R, G, and B values for a purely black surface should all be 0, whereas for an ideal purely white surface, each of these three values should be equal to a predefined maximum value. The maximum value is equal to $2^n-1$, wherein n is the number of bits defining a pixel. If an 8-bits pixel depth is used, this maximum value is 255.

When metallic coatings are examined, the lightness can exceed the lightness of white locally. This should be taken into account, for example by choosing a maximum white value lower than $2^n-1$.

For accurate colour measurement, it is preferred to calibrate the measurements periodically. When a CCD camera is used, calibration can for example be carried out by first separately recording a black sample and a white sample. The R,G,B values of the black value are subtracted from the R, G, and B values of the white sample and of the measured sample in question. Subsequently, the R, G, and B values of the measured sample are divided by the corresponding values of the white calibration sample and are multiplied with the maximum white value. This means that for every pixel in the image, a calibrated value $R_{cal}$ of the R value is calculated using the following formula:

$$R_{cal}=255*(R-R_{black})/(R_{white}-R_{black})$$

In this formula, $R_{black}$ is the R value of a pixel in the black sample, whereas $R_{white}$ is the R value of a pixel in the white sample. Calibrated values for the B and G values are calculated correspondingly. This correction accounts for deviations in the light sensitivity of the pixels and for the variation in illuminant intensity as a function of optical geometry. Optionally, the R, G, and B values can be corrected for time-dependent variations in light intensity. This can be done for example by applying a parallel white strip to the sample. For calculation purposes, the sample and the white strip are considered to be divided along the longitudinal axis of the sample by a large number of virtual parts. For every sample part, the average R, G, and B values $R_{av}$, $G_{av}$, and $B_{av}$ are determined. Similarly, for every white strip part, the average R, G, and B values $R_{white-av}$, $G_{white-av}$, and $B_{white-av}$ are determined. The corrected R value $R_{cor}$ for each sample part is then calculated using the following formula:

$$R_{cor}=255*(R_{av}/R_{white-av}).$$

$G_{cor}$ and $B_{cor}$ are calculated accordingly.

The most common systems for calorimetric data have been laid down by the Commission International de l'Eclairage (CIE), e.g., CIELab (L*, a*, b*), CIEXYZ (X, Y, Z), and CIELuv (L*, u*, v*). These systems take the sensitivity of the human eye into account. The R, G, and B values, as measured by a CCD camera, can be converted to L*, a*, b* values of the CIELab system.

The mathematical model selected may be any model known to the skilled person. Examples are mentioned in H. R. Kang, *Color Technology for Electronic Imaging Devices*, SPIE Optical Engineering Press, 1997, chapters 3 and 11, and in U.S. Pat. No. 5,850,472. The model may be non-linear or linear. One example of a non-linear model is a $2^{nd}$ order polynomial having 10 parameters or a $3^{rd}$ order polynomial having 20 parameters. Preferably, use is made of a linear model. More preferably, the linear model used has 4 model parameters.

One example of a linear model having 4 parameters is the following model, where the measured colour signals of the calibration colours, in this case R, G, and B data, are converted to colorimetric data, in this case CIELab data:

$$L_i^*=c_0+c_1R_i+c_2G_i+c_3B_i$$

$$a_i^*=d_0+d_1R_i+d_2G_i+d_3B_i$$

$$b_i^*=e_0+e_1R_i+e_2G_i+e_3B_i$$

wherein $R_i$, $G_i$, $B_i$ are the measured signals and $L_i^*$, $a_i^*$, and $b_i^*$ are the colorimetric data of calibration colour i.

Linear regression is used to calculate the 12 model parameters $C_0$–$C_3$, $d_0$–$d_3$, and $e_0$–$e_3$ from the measured RGB data and the known CIELab data (CIE 1964 standard colorimetric observer) of the calibration colours. These model parameters are used to convert the measured RGB data of the selected colour to CIELab data.

One example of a non-linear $3_{rd}$ order polynomial having 20 parameters is:

$$L_i^*=c_0+c_1R_i+c_2G_i+c_3B_i+c_4R_i^2+c_5G_i^2+c_6B_i^2+c_7R_iG_i+\\c_8R_iB_i+c_9G_iB_i+c_{10}R_i^3+c_{11}G_i^3+c_{12}B_i^3+c_{13}R_i^2G_i+\\c_{14}R_i^2B_i+c_{15}G_i^2R_i+c_{16}G_i^2B_i+c_{17}B_i^2R_i+c_{18}B_i^2G_i+\\c_{19}R_iG_iB_i$$

$$a_i^*=d_0+d_1R_i+d_2G_i+d_3B_i+d_4R_i^2+d_5G_i^2+d_6B_i^2+d_7R_iG_i-\\d_8R_iB_i+d_9G_iB_{i+d10}R_i^3+d_{11}G_i^3+d_{12}B_i^3+d_{13}R_i^2G_i+\\d_{14}R_i^2B_i+d_{15}G_i^2R_i+d_{16}G_i^2B_{i+d17}B_i^2R_i+d_{18}B_i^2G_i+\\d_{19}R_iG_iB_i$$

$$b_i^*=e_0+e_1R_i+e_2G_i+e_3B_i+e_4R_i^2+e_5G_i^2+e_6B_i^2+e_7R_iG_i-\\e_8R_iB_i+e_9G_iB_i+e_{10}R_i^3+e_{11}G_i^3+e_{12}B_i^3+e_{13}R_i^2G_i+\\e_{14}R_i^2B_i+e_{15}G_i^2R_i+e_{16}G_i^2B_i+e_{17}B_i^2R_i+e_{18}B_i^2G_i+\\e_{19}R_iG_iB_i$$

Linear regression is used to calculate the 60 model parameters $c_0$–$c_{19}$, $d_0$–$d_{19}$, and $e_0$–$e_{19}$ from the measured RGB data and the known CIELab data of the calibration colours. These model parameters are used to convert the measured RGB data of the selected colour to CIELab data.

Notwithstanding the above, it is possible to lend greater weight to the calibration colours in the vicinity of the selected colour when calculating the model parameters. In the case of the above example of a linear model having 4 parameters, this means that during the linear regression each calibration colour is given a weighting factor based on the distance in the RGB colour space between the calibration colour in question and the selected colour. In the linear regression procedure the following sum of squares is minimized:

$$\sum_{i=1}^{n} w_i(y_i-\hat{y}_i)^2$$

wherein $w_i$ is a weighting factor, $y_i$ is the $L_i^*$, $a_i^*$, or $b_i^*$ based on spectral measurements and $\hat{y}_i$ is the calculated value for $L_i^*$, $a_i^*$, or $b_i^*$ based on the RGB to CIELab conversion.

With $\hat{y}_i$ being equal to $c_0+c_1R+c_2G+c_3B$ (see above), and $w_i$ being equal to $((R_1-R)^2+(G_1-G)^2+(B_1-B)^2)^{-2}$, this sum is as follows:

$$\sum_{i=1}^{n} (L_i^* - c_0 - c_1R_i - c_2G_i - c_3B_i)^2((R_i-R)^2+(G_i-G)^2+(B_i-B)^2)^{-2}$$

$$\sum_{i=1}^{n} (a_i^* - d_0 - d_1R_i - d_2G_i - d_3B_i)^2((R_i-R)^2+(G_i-G)^2+(B_i-B)^2)^{-2}$$

$$\sum_{i=1}^{n} (b_i^* - e_0 - e_1R_i - e_2G_i - e_3B_i)^2((R_i-R)^2+(G_i-G)^2+(B_i-B)^2)^{-2}$$

wherein n : is the number of calibration colours

R, G, B: are the measured signals of the selected colour

Alternatively, it is possible to use the calibration colours in the vicinity of the selected colour for interpolation. If so desired, grey balancing may be performed on the signals measured for black, white, and grey according to the formula $R=G=B=f(L^*)$ or a comparable value for $L^*$ in a different calorimetric system. Such grey balancing is described in H. R. Kang, *Color Technology for Electronic Imaging Devices*, SPIE Optical Engineering Press, 1997, chapter 11.

Using image processing software, such as the computer program Optimas® commercially available from Media Cybernetics, or the program Image ProPlus® available from the same company, individual particles can be identified by recognition of differing luminance relative to the particle's background. These particles can for instance be metallic pigments or clusters of metallic pigments. After identification of the particles, the number of particles, and image parameters like particle size, particle shape, the length of the shortest and the longest axis, as well as the R, G, and B values of the particles can be determined by the image processing software. This data optionally can be averaged per strip part, or per larger part if so required.

The data determined on the basis of the images can for example be used to search for a coating formulation giving a matching surface coating. To this end, the measured data can be compared with data from a colour formulation database.

To enhance the scope of the imaging device, the light source can optionally comprise a set of mirrors. It has been found that using mirrors in a suitable arrangement can enhance the scope to about 90 degrees or even more.

Although the light source may be a permanent light source, a flash light is preferred to minimize the use of energy. If permanent light sources are used, the camera should be set at a suitable exposure time. Suitable light sources are for instance tungsten halogen lamps or xenon lamps.

In a particularly preferred embodiment, the light source comprises a light diffusing housing discharging light via a slit. The longitudinal side of the slit is arranged substantially parallel to the sample surface, whereas the short side is substantially perpendicular to the sample surface. In such an arrangement, a light sensor can be used to control the light output. In a preferred embodiment of such a diffusor, the slit is bordered by a substantially horizontal wall at the inner side of the diffusor. This way, the light intensity at the sample surface is a function of the flop angle. On positions at a smaller angular distance to the diffusor, the light intensity is less than at larger angles.

In a further preferred embodiment of the device according to the present invention, the spectral distribution of the light is varied in one image as a function of the position on the sample, e.g., by using different light sources or using a set of filters, a grating, or a prism. This enhances the number of independent measurement data and thus improves colour accuracy. This can be done for example by varying the light from the light source or by varying the spectral distribution of the light just before it enters the imaging device. Preferably, the spectral distribution of the illumination is varied perpendicular to the variation of optical geometry.

To eliminate any effect of environmental light, the device according to the invention preferably comprises a housing.

The present invention includes a method of surface evaluation as described above wherein, in general, the recorded light interaction is the light reflection of a sample. However, if the sample is transparent or semi-transparent, the recorded light interaction can be light transmission. In that case, the sample is positioned between the imaging device and the light source.

Flat samples can be used. However, if so required, curved samples may also be suitable for the examination of flop behaviour.

Figure 4:
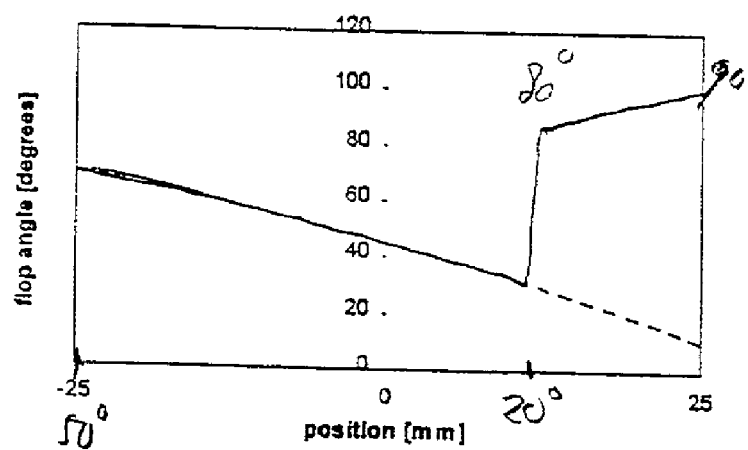
Figure 2:
Figure 3:
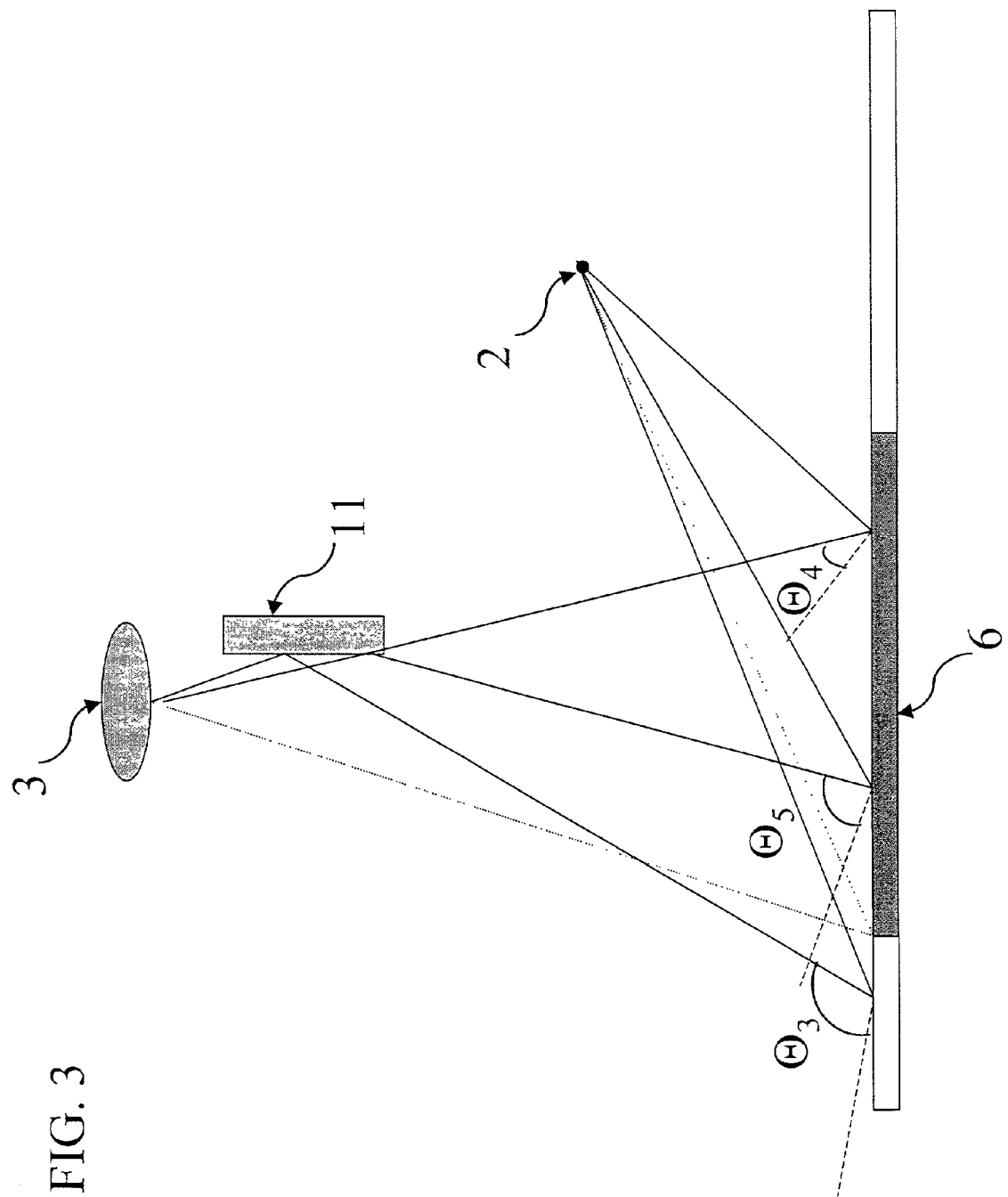
Figure 6:
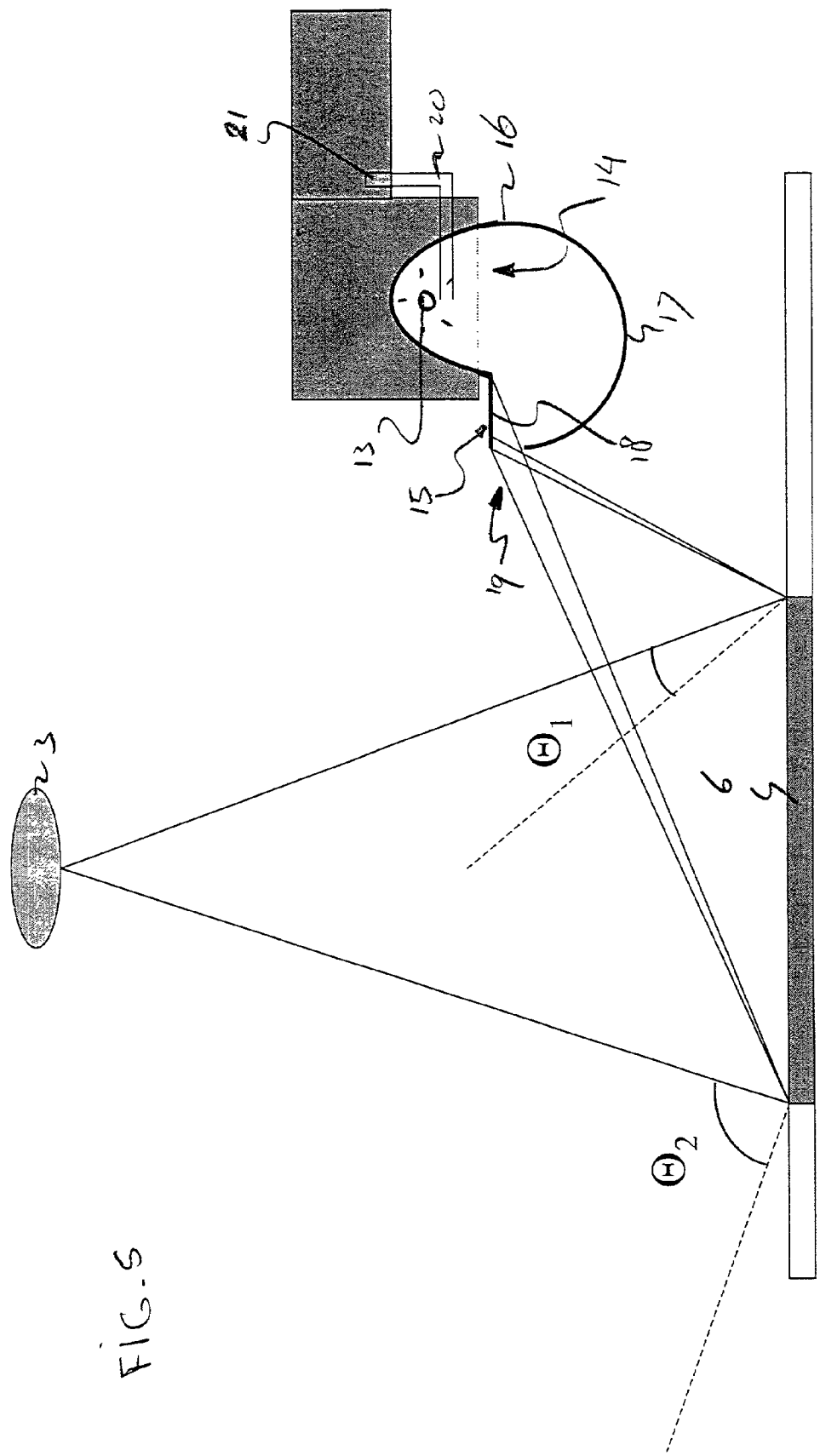
Figure 7:
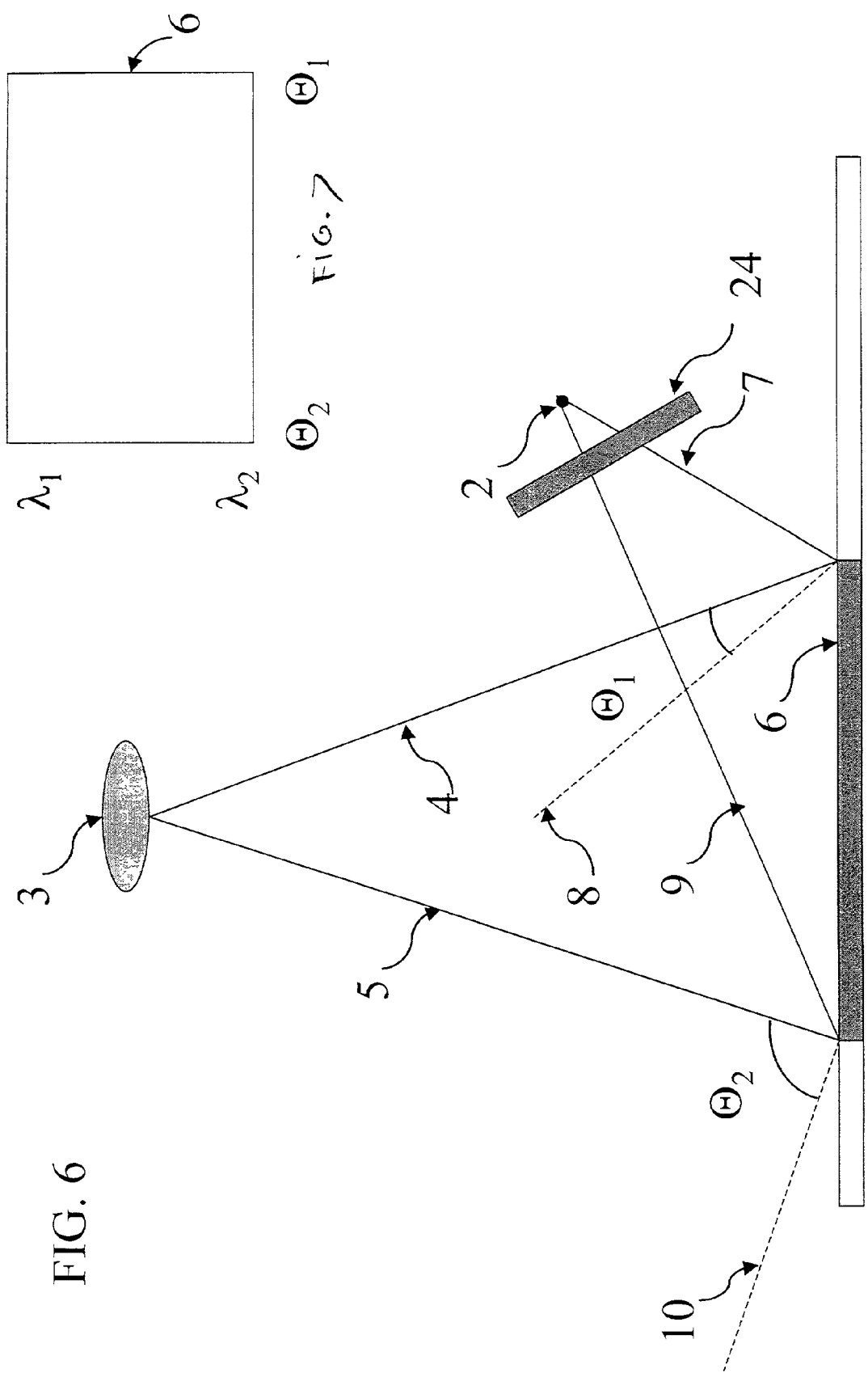
Figure 8:
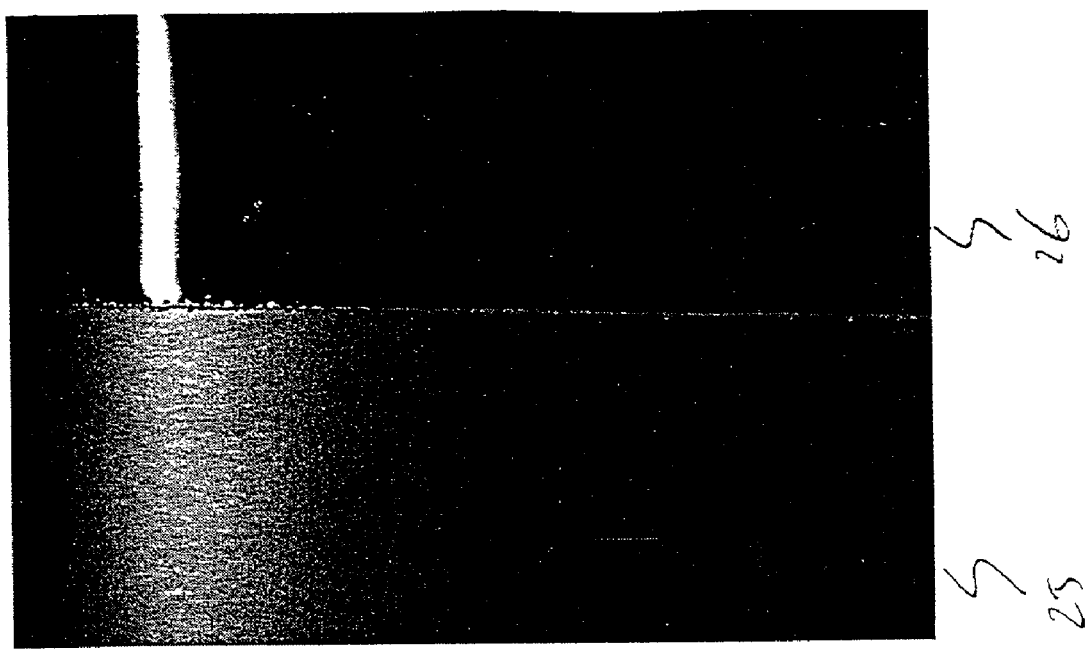

The invention is further described and illustrated by the drawings. In the drawings:

FIG. 1: shows a schematic overview of a recording arrangement according to the invention;

FIG. 2: shows a recording by the arrangement of FIG. 1;

FIG. 3: shows schematically an alternative arrangement according to the invention;

FIG. 4: shows a plot of the flop angle as a function of the position, as recorded by the arrangement of FIG. 3;

FIG. 5: shows a third alternative arrangement according to the invention;

FIG. 6: shows a fourth alternative embodiment of the invention;

FIG. 7: shows the change in the filtered wavelength ranging over a sample imaged in a device according to FIG. 6.;

FIG. 8: shows a sample with a parallel reference sample for gloss measurement.

FIG. 1 shows an arrangement 1 according to the present invention, comprising a light source 2, a CCD camera 3 as a recording device, having a viewing angle a ranging from a first outer end observation direction 4 closest to the light source to a second outer end observation direction 5. A coated sample 6 is located under the camera 3. The light source 2 is a line source parallel to the sample surface. The light source 2 is located outside the direct scope of the CCD camera 3. The line between the light source 2 and the point where the observation direction 4 meets the sample 6 defines a first illumination direction 7, which is reflected by the sample 6 in a direction defined as the first specular direction 8. Similarly, the line between the light source 2 and the point where the observation direction 5 meets the sample 6 defines a second illumination direction 9, which is reflected by the sample 6 in a direction defined as the second specular direction 10. In the drawing, the outer flop angle $\Theta_1$ is the angle between the first observation direction 4 and the first specular direction 8, whereas the outer flop angle $\Theta_2$ is the angle between the second observation direction 5 and the second specular direction 10. The angular range between $\Theta_1$ and $\Theta_2$ may span up to about 90 degrees.

FIG. 2 shows a recorded image recorded by the arrangement of FIG. 1. It is the image of a sample coated with a metallic paint. The figure shows how brightness varies with the flop angle. The image in FIG. 2 also shows a change in coarseness over the length of the sample, as would also be experienced by the human eye.

FIG. 3 shows an alternative arrangement according to the invention, where the flop angle scope is enhanced by the use of a mirror 11. The mirror 11 is arranged in such a way that it reflects the sample part right next to the outer end of the camera's viewing angle scope most distant from the light source 2. In the image observed by the camera 3, the scope closest to the light source 2 is replaced by an extension of the scope on the other side. From right to left, the recording shows the scope from $\Theta_3$ to $\Theta_5$ and subsequently the scope from $\Theta_4$ to $\Theta_2$. The scope from $\Theta_1$ to $\Theta_4$ is not visible anymore on the recording.

FIG. 4 shows the flop angle as a function of the position in an arrangement similar to the arrangement of FIG. 3, position 0 being right under the camera. The mirrored part of the sample overlaps the part from about 20 mm to 25 mm.

Optionally, the sample can be recorded in two (or even more) separate parallel strips, one with a mirror enhanced scope and the other without. This way, the full enlarged scope ranging from $\Theta_1$ to $\Theta_2$ and the scope ranging from $\Theta_5$ to $\Theta_3$ can be recorded. If $\Theta_5$ is equal to $\Theta_2$, then a closed range from $\Theta_1$ $\Theta_3$ is covered.

FIG. 5 shows an arrangement similar to the arrangement of FIG. 1 with a camera 3 right above a sample 6 where a light source 12 comprises a standard flash light 13, available under the trademark Metz 45CT-1. The flash light 13 comprises a transparent side 14. At the transparent side 14, the flash light is connected to the flat upper side 15 of a diffusor 16 comprising a semi-cylindrical part 17. This flat side 15 is open where it is in connection with the transparent side 14 of the flash light 13. The inner side of the diffusor 16 is covered with a white coating. Where it does not coincide with the transparent side 14 of the flash light 13, the flat side 15 is closed by a horizontal wall 18, which on its inside is provided with a white coating. The edge between the outer end of the horizontal wall 18 and the semi-cylindrical part 17 is provided with a vertical slit 19 extending over the width of the diffusor 16.

When the flash light 13 flashes, the light is diffused by the reflective coatings at the inner side of the diffusor 16. Part of the light is reflected by the reflective layer of the horizontal wall 18 through the slit 19 onto the part of the sample 6 to be imaged. As can be seen in FIG. 5, at the outer viewing direction of the camera's viewing angle scope closest to the diffusor 16, the sample 6 is illuminated by a considerably smaller part of the reflective horizontal wall 17 than at the camera's outer viewing direction distant from the diffusor 16. This way, the light density is a function of the angular distance from the light source. The function can be varied with the orientation of the slit with respect to the sample surface.

A glass fibre cable 20 connects the space enclosing the flash light 13 to a light sensor 21 controlling the time interval at which the flash light 13 flashes. Part of the light diffused in the diffusor 16 escapes via the glass fibre cable 20 to the light sensor 21. The quantity of light passing the glass fibre cable 20 is measured by the light sensor 21. When a pre-defined quantity of light has passed the glass fibre cable 20, the sensor 21 stops the flash light 13. This way, it is ensured that every flash gives exactly the same quantity of light.

FIG. 6 shows a further alternative embodiment of a device according to the invention, comprising an imaging device 3 and a light source 2. A sample 6 is located under the imaging device 3. A set of filters and a grating or a prism 24 are positioned between the light source 2 and the sample 6. The spectral distribution of the illumination is varied in one image as a function of the position on the sample. FIG. 7 shows the result of the preferred embodiment where the spectral distribution of the illumination is varied perpendicular to the variation of optical geometry.

FIG. 8 shows that the gloss behaviour of a sample can be wherein as a function of optical geometry. This particular example shows in one image the difference between a high gloss sample 25 and a low gloss sample 26.

The invention claimed is:

1. A method for recording goniochromatic propertries of a paint film using an imaging device for recording light interaction with a surface, a light source, and a sample area for positioning a sample with a paint film to be examined, wherein the imaging device, the light source, and the sample area are arranged in a triangular arrangement for recordal in one image of at least one of the goniochromatic properties of the paint film as a function of a continuous range of flop angles between the specular direction and the observation direction.

2. The method according to claim 1, wherein the flop angle is more than 40 degrees.

3. The method according to claim 1, wherein the light intensity by the light source varies over the scope of the imaging device.

4. The method according to claims 1, wherein light source is a line source.

5. The method according to claim 1, wherein the imaging device is a CCD camera.

6. The method according to claim 1, wherein the device comprises a set of mirrors enhancing the scope of the imaging device.

7. The method according to claim 1, wherein the light source is a flash light comprising a light output control.

8. The method according to claim 1, wherein the device comprises a set of filters and a grating or a prism for variation of the spectral distribution of the illumination or the spectral distribution of the light entering the recording device as a function of the position on the sample.

9. The method according to claim 1, wherein one of the goniochromatic propertries is the gloss of the sample.

10. The method according to claim 1, wherein the recorded light interaction is the light reflection of a sample.

11. The method according to claim 10, wherein the recorded light interaction is the light transmission of a semi-transparent sample.

* * * * *